(12) United States Patent
McGill et al.

(10) Patent No.: US 9,623,204 B2
(45) Date of Patent: Apr. 18, 2017

(54) ELECTROLYSIS SYSTEM AND APPARATUS FOR COLLECTING HYDROGEN GAS

(71) Applicant: Hydro Healer, LLC, Cedar City, UT (US)

(72) Inventors: Bruce J McGill, Cedar City, UT (US); Stephen Doughty, Toquerville, UT (US); Tim Nieman, Salt Lake City, UT (US)

(*) Notice: Subject to any disclaimer, the term of this patent is extended or adjusted under 35 U.S.C. 154(b) by 573 days.

(21) Appl. No.: 13/971,693

(22) Filed: Aug. 20, 2013

(65) Prior Publication Data

US 2014/0048067 A1    Feb. 20, 2014

Related U.S. Application Data

(60) Provisional application No. 61/691,021, filed on Aug. 20, 2012.

(51) Int. Cl.
*A61M 16/10* (2006.01)
*A61M 15/00* (2006.01)
(Continued)

(52) U.S. Cl.
CPC ............ *A61M 16/10* (2013.01); *A61M 15/00* (2013.01); *A61M 15/0086* (2013.01); *C25B 1/04* (2013.01);
(Continued)

(58) Field of Classification Search
CPC ............ A61M 15/00; A61M 15/0086; A61M 15/0006; A61M 16/10; A61M 16/12;
(Continued)

(56) References Cited

U.S. PATENT DOCUMENTS 3,971,372 A * 7/1976 Lenk .................. A62B 21/00
                                                128/202.26
4,016,065 A * 4/1977 Beck .................... C25B 1/02
                                                204/228.5
(Continued)

FOREIGN PATENT DOCUMENTS

JP          08-176873 A      7/1996

OTHER PUBLICATIONS

Ikuroh Ohsawa, et al., Hydrogen Acts as a Therapeutic Antioxidant by Selectively Reducing Cytotoxic Oxygen Radicals, Nature Publishing Group http://www.nature.com/naturemedicine, May 7, 2007.

(Continued)

*Primary Examiner* — Lynne Anderson
*Assistant Examiner* — Elliot S Ruddie
(74) *Attorney, Agent, or Firm* — Kunzler Law Group

(57) ABSTRACT

The present disclosure relates to an electrolysis apparatus that includes an anode electrically connectable to a direct current electrical source. The apparatus also includes a cathode comprising a proximal segment and a distal segment. The proximal segment is electrically connectable to the direct current electrical source. Further, the apparatus includes a hydrogen collector receptacle that limits generation and collection of hydrogen at the cathode to a specified amount. The hydrogen collector receptacle encompasses a portion of the cathode. Also, the apparatus includes a delivery device that receives hydrogen from and is connected to the hydrogen collector receptacle. According to one embodiment, the hydrogen gas generated in the electrolysis apparatus and collected in the collector receptacle is less than about 4.5% of a user's breath.

18 Claims, 13 Drawing Sheets

(51) Int. Cl.
*C25B 1/04* (2006.01)
*C25B 11/02* (2006.01)
*C25B 15/08* (2006.01)
*C25B 9/06* (2006.01)
*A61M 16/06* (2006.01)
*H01M 8/0656* (2016.01)

(52) U.S. Cl.
CPC ............... *C25B 9/06* (2013.01); *C25B 11/02* (2013.01); *C25B 15/08* (2013.01); *A61M 15/0006* (2014.02); *A61M 16/0666* (2013.01); *H01M 8/0656* (2013.01); *Y02E 60/366* (2013.01)

(58) Field of Classification Search
CPC ............ A61M 16/1005; A61M 16/06; A61M 16/0666; C25B 1/02; C25B 1/04; C25B 9/06; C25B 11/02; C25B 15/08; Y02E 60/366; H01M 8/0656
USPC ............ 128/202.26, 203.12, 203.14, 203.16, 128/203.22, 203.25, 203.29; 204/157.5, 204/157.52, 228.1, 228.6, 232, 242, 263, 204/266, 275.1, 278
See application file for complete search history.

(56) References Cited

U.S. PATENT DOCUMENTS

| | | | |
|---|---|---|---|
| 4,016,878 A * | 4/1977 | Castel | A61M 16/1075 126/204 |
| 4,356,076 A | 10/1982 | Matsushita et al. | |
| 7,156,962 B2 | 1/2007 | Koizumi et al. | |
| 2003/0079749 A1 * | 5/2003 | Strickland | A61M 16/0666 128/203.22 |
| 2006/0003203 A1 | 1/2006 | Wang et al. | |
| 2006/0011489 A1 | 1/2006 | Swanepoel et al. | |
| 2007/0217995 A1 | 9/2007 | Matsumura et al. | |
| 2009/0035383 A1 * | 2/2009 | Ohta | A23L 1/30 424/600 |
| 2009/0071472 A1 | 3/2009 | Cohen et al. | |
| 2009/0129992 A1 * | 5/2009 | Mills | B01J 19/087 422/112 |
| 2009/0169933 A1 | 7/2009 | Okuyama et al. | |
| 2010/0104904 A1 * | 4/2010 | Rao | C25B 1/02 429/412 |
| 2010/0133108 A1 | 6/2010 | Hsu et al. | |
| 2010/0155258 A1 | 6/2010 | Kirk et al. | |
| 2010/0330547 A1 | 12/2010 | Tempelman et al. | |
| 2011/0132367 A1 * | 6/2011 | Patel | A61M 16/12 128/204.22 |
| 2011/0257275 A1 | 10/2011 | McAlister | |

OTHER PUBLICATIONS

Cai, et al., Hydrogen Therapy Reduces Apoptosis in Neonatal Hypoxia-Ischennia Rat Model, Neuroscience Lettters—journal homepage: www.elsevier.com/locate/neulet, 2008.

Fukuda, et al., Inhalation of hydrogen gas suppresses hepatic injury caused by ischennia/reperfusion through reducing oxidative stress, ScienceDirect, www.elsevier.com/locate/ybbrc, Jul. 25, 2007.

Koshu, et al., Measurement of regional blood flow using hydrogen gas generated by electrolysis, stroke. ahajournals.org—Stroke vol. 13, 483-487, 1982.

PCT/US2013/055890, International Search Report & Written Opinion, Nov. 20, 2013.

* cited by examiner $H_2O \Rightarrow \tfrac{1}{2}O_2 + 2H^+ + 2e^-$  $\qquad$  $2H_2O + 2e^- \Rightarrow H_2 + 2OH^-$ $2OH^- \Rightarrow \tfrac{1}{2}O_2 + H_2O + 2e^-$  $\qquad$  $2H^+ + 2e^- \Rightarrow H_2$ $2H_2O \Rightarrow O_2 + 2H_2$

ELECTROLYSIS SYSTEM AND APPARATUS FOR COLLECTING HYDROGEN GAS

CROSS-REFERENCES TO RELATED APPLICATIONS

This application claims the benefit of U.S. Provisional Patent Application No. 61/691,021 entitled "Electrolysis System and Apparatus for Collecting Hydrogen Gas" and filed on Aug. 20, 2012 for Bruce McGill et al., which is incorporated herein by reference.

FIELD

This disclosure relates to electrolysis systems and more particularly relates to the generation and collection of hydrogen from the electrolysis of aqueous solutions.

BACKGROUND

Cells are the basic structural and functional units of all living organisms. Generally, cells operate by interacting with various chemical elements to produce desired results. For example, the mitochondria organelles in cells chemically convert sugar, fat, and protein into adenosine triphosphate ("ATP"), which can then be transferred to other cells and consumed to provide energy to the organism. Thus, cells are constantly participating in biochemical reactions in order to carry-out specific functions. Often, cell function and performance is regulated by balancing competing chemical reactions. For example, reduction and oxidation ("redox") type reactions must be balanced in order to maintain a healthy cellular environment and to prevent the build-up of potentially harmful oxidized species. Additionally, intermediary products of chemical reactions, if not neutralized, can also create toxic cellular environments which can damage or ultimately kill cells.

One specific example of cellular damage, known as oxidative stress, occurs when cells are unable to properly regulate redox reactions and the resultant reactive oxygen species (ROS—i.e., peroxides and free radicals) damage components of the cell. While some damage may be reversible, other damage is permanent, such as the deformation or destruction of a cell's DNA. Traditionally, oxidative stress has been combated through the use of reducing agents and antioxidants. Antioxidants help to neutralize the ROS and help to restore cells to their proper balance. One example of a chemical that has been implemented as an antioxidant is hydrogen. Not only is hydrogen an effective antioxidant, hydrogen can also be an effective therapeutic agent to combat inflammation and apoptosis in cells.

Hydrogen has been used to neutralize ROS and to promote the proper redox balance in cells. Conventionally, hydrogen has been introduced into the human body by drinking water that contains dissolved hydrogen or by injecting a hydrogen-saturated saline solution into the bloodstream. While these methods may be somewhat effective, inhalation of hydrogen gas is especially effective and efficient because the hydrogen gas can enter the blood stream through the thin membrane in the lungs. However, hydrogen gas is conventionally stored and transported in compressed and high pressure containers. These pressurized sources of hydrogen gas can be dangerous because hydrogen gas is flammable at concentrations of about 4%.

SUMMARY

From the foregoing discussion, it should be apparent that a need exists for an apparatus and system that overcomes the above discussed shortcomings of conventional hydrogen therapy systems. Beneficially, such an apparatus and system would provide for the safe inhalation of hydrogen gas.

The subject matter of the present application has been developed in response to the present state of the art, and in particular, in response to the problems and needs in the art that have not yet been fully solved by currently available hydrogen therapy systems. Accordingly, the present disclosure has been developed to provide an apparatus and system for generating breathable levels of hydrogen gas that overcome many or all of the above-discussed shortcomings in the art.

The present disclosure relates to an electrolysis apparatus that includes an anode electrically connectable to a direct current electrical source. The apparatus also includes a cathode comprising a proximal segment and a distal segment. The proximal segment is electrically connectable to the direct current electrical source. Further, the apparatus includes a hydrogen collector receptacle that controls the collection of hydrogen at the cathode. The hydrogen collector receptacle encompasses a portion of the cathode. Also, the apparatus includes a delivery device that receives hydrogen from and is connected to the hydrogen collector receptacle. According to one embodiment, the hydrogen gas generated in the electrolysis apparatus and collected in the collector receptacle is less than about 4.5% of a user's breath.

In one embodiment, the hydrogen collector receptacle circumferentially encompasses a portion of the cathode and has an aperture near the distal segment of the cathode. The aperture of the hydrogen collector receptacle may have a valve that that is configurable to have various cross-sectional areas. The apparatus may also further include an ion flow limiter module that controls the rate of electrolysis, wherein the ion flow limiter module comprises a wall between the cathode and the anode that partially restricts the flow ions between the cathode and the anode. In one embodiment, the wall is a perforated separating wall that restricts the flow of ions between the cathode and the anode. In further implementations, the apparatus may also include an electric control module that controls the rate of electrolysis. The apparatus may also have a flow chamber interconnected between the hydrogen collector receptacle and the delivery device, wherein the flow chamber controls the transfer of hydrogen from the hydrogen collector receptacle to the delivery device. The flow chamber introduces and combines a delivery fluid with the collected hydrogen to control the concentration of hydrogen transferred to the delivery device. The amount of hydrogen gas transferred to the delivery device is less than about 4.5% of a user's breath, according to one implementation. The delivery device may include one or more cannula tubing, a mask respirator, an inhaler device, a storage chamber, and a gas emitter. Also, at least a portion of one or more of the cathode and the anode may include a metallic mesh, such as copper mesh or stainless steel mesh.

The present disclosure also relates to an electrolysis system that includes a vessel containing an electrolyte solution. Further, the system includes an anode electrically connectable to a direct current electrical source, wherein at least a portion of the anode is in fluid contact with the electrolyte solution. Still further, the system includes a cathode that has a proximal segment and a distal segment, wherein the proximal segment is electrically connectable to the direct current electrical source and the distal segment is in fluid contact with the electrolyte solution. Also, the system includes a hydrogen collector receptacle that controls the collection of hydrogen at the cathode, wherein the hydrogen collector receptacle encompasses a portion of the cathode and a delivery device that receives hydrogen from and is connected to the hydrogen collector receptacle.

According to one embodiment, the system may also include an electrolyte temperature control module for controlling the temperature of the electrolyte. The electrolyte temperature control module may be an outer vessel that is configured to control the temperature of the electrolyte in the electrolyte vessel. Further, the electrolyte solution may contain a salt, such as sodium bicarbonate, to facilitate the electrolysis reaction.

The present disclosure also relates to an electrolysis method for generating hydrogen. The method includes providing an anode in fluid contact with an electrolyte solution and electrically connected to a direct current electrical source. The method also includes providing a cathode in fluid contact with the electrolyte solution and electrically connected to the direct current electrical source. Further, the method includes providing a hydrogen collector receptacle encompassing a portion of the cathode. The method also includes limiting the generation and collection of hydrogen at the cathode to a specific amount by restricting the flow of ions in the electrolyte solution to and from the cathode with the hydrogen collector receptacle. Additionally, the method includes providing a delivery device that is connected to the hydrogen collector receptacle. Further, the method includes transferring hydrogen collected in the hydrogen collector receptacle to the delivery device.

Reference throughout this specification to features, advantages, or similar language does not imply that all of the features and advantages that may be realized with the present disclosure should be or are in any single embodiment of the invention. Rather, language referring to the features and advantages is understood to mean that a specific feature, advantage, or characteristic described in connection with an embodiment is included in at least one embodiment of the subject matter disclosed herein. Thus, discussion of the features and advantages, and similar language, throughout this specification may, but do not necessarily, refer to the same embodiment.

Furthermore, the described features, advantages, and characteristics of the disclosure may be combined in any suitable manner in one or more embodiments. One skilled in the relevant art will recognize that the subject matter of the present application may be practiced without one or more of the specific features or advantages of a particular embodiment. In other instances, additional features and advantages may be recognized in certain embodiments that may not be present in all embodiments of the disclosure. Further, in some instances, well-known structures, materials, or operations are not shown or described in detail to avoid obscuring aspects of the subject matter of the present disclosure. These features and advantages of the present disclosure will become more fully apparent from the following description and appended claims, or may be learned by the practice of the disclosure as set forth hereinafter.

BRIEF DESCRIPTION OF THE DRAWINGS

In order that the advantages of the disclosure will be readily understood, a description of the disclosure will be rendered by reference to specific embodiments that are illustrated in the appended drawings. Understanding that these drawings depict only typical embodiments of the disclosure and are not therefore to be considered to be limiting of its scope, the subject matter of the present application will be described and explained with additional specificity and detail through the use of the accompanying drawings, in which.

DETAILED DESCRIPTION

Reference throughout this specification to "one embodiment," "an embodiment," or similar language means that a particular feature, structure, or characteristic described in connection with the embodiment is included in at least one embodiment of the present disclosure. Thus, appearances of the phrases "in one embodiment," "in an embodiment," and similar language throughout this specification may, but do not necessarily, all refer to the same embodiment.

Furthermore, the described features, structures, or characteristics of the disclosure may be combined in any suitable manner in one or more embodiments. In the following description, numerous specific details are provided. One skilled in the relevant art will recognize, however, that the subject matter of the present application may be practiced without one or more of the specific details, or with other methods, components, materials, and so forth. In other instances, well-known structures, materials, or operations are not shown or described in detail to avoid obscuring aspects of the disclosure.

Figure 1:
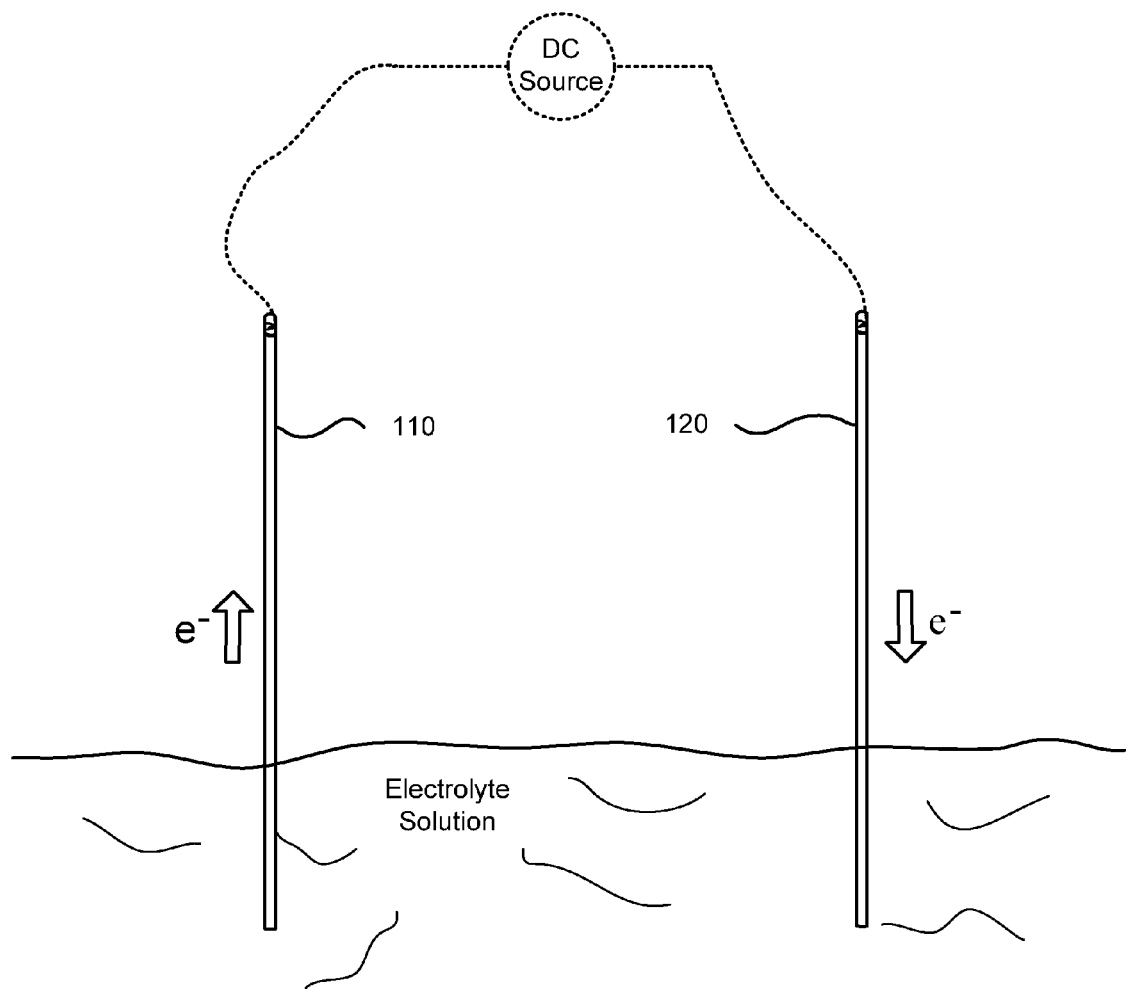
FIG. 1 depicts an aqueous electrolysis reaction, according to one embodiment.

FIG. 1 depicts one embodiment of an aqueous electrolysis reaction. Electrolysis of water is the decomposition of water into hydrogen and oxygen gas. The anode 110 and the cathode 120 (collectively the "electrodes") are metallic materials. These metallic electrodes may be connected to an electrical current source and a portion of the electrodes may be placed into an aqueous solution ("electrolyte solution").

The electric current passes through the electrolyte solution via ions, thereby completing the circuit. Generally the subject matter of the present application relates to the non-spontaneous electrolysis of an aqueous electrolyte and the collection of the gaseous products that are generated through reduction at the cathode 120. Conventionally in electrolytic cells, the cathode 120 is negatively charged and the anode 110 is positively charged.

The schematic flow chart diagrams included herein are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

The flow of electrons out of the cathode 120 and into the electrolyte solution causes electrochemical reduction reactions. Reduction reactions involve reducing the oxidation state of a given molecule. In other words, electrons combine with certain components in the electrolyte solution that are near the cathode 120. Once the electrons leaving the cathode 120 have combined with the nearby molecules and/or ions ("reduced components"), the reduced components then move across the charge concentration gradient towards the anode 110.

At the anode 110, the electrons are released from various molecules and ions in the electrolyte solution through electrochemical oxidation reactions. Oxidation reactions involve increasing the oxidation state of a given molecule. In other words, electrons separate from the components in the electrolyte solution that are near the anode 110. Once the electrons have left the components and moved "into" the anode 110, the oxidized components then move across the charge concentration gradient back towards the cathode 120. Thus, the continual back and forth movement by various ions and molecules in the electrolyte solution completes the circuit in an electrolytic cell.

Also, the reduction and oxidation reactions ("Redox" reactions), in one embodiment, produce gaseous-phase components that tend to flow upwards and out of the electrolyte solution. For example, in FIG. 1 various electrochemical half reactions are shown that illustrate one embodiment of the types of reduction and oxidation reactions that may occur in an aqueous electrolyte. The half-reactions near the anode 110 involve oxidizing water and hydroxide ions to produce gaseous oxygen. The half-reactions at the cathode 120 involve reducing water and hydrogen ions to produce gaseous hydrogen. After adding the two half reactions at the anode 110 with the two half reactions at the cathode 120, the overall reaction of the electrolytic cell is the decomposition of liquid water into gaseous hydrogen and oxygen. While various byproducts are also produced during electrolysis, the main reaction is the one depicted in FIG. 1.

Although pure water may be used as a the electrolyte solution, generally a salt is dissolved into water, thus promoting the electrolysis reaction by creating an ionized aqueous solution that more efficiently transfers electrons from the cathode 120 to the anode 110. For example, a sodium bicarbonate aqueous solution may function as the electrolyte solution. In one embodiment, the electrolyte solution is substantially free of toxic chemicals so that any gaseous products of the redox reactions are substantially safe for direct user respiration. When salts are used, various other half-reactions occur and different byproducts are produced, but water is still separated into hydrogen and oxygen. As recognized by those of ordinary skill in the art, it is contemplated that other salts and chemicals may be used in the electrolyte solution.

As briefly described above, the electrodes 110, 120 are made from materials that are capable of conducting electricity. For example, in one embodiment the anode 110 includes a stainless steel rod and the cathode 120 includes a copper rod. It is contemplated that other metals, such as iron, zinc, cobalt, chromium, nickel, and the like, may be used in the electrolysis apparatus of the present disclosure. In one embodiment, the metals used for the cathode 120 and the anode 110 are selected according to the level of toxicity. For example, non-toxic electrodes may be especially useful for producing non-toxic hydrogen gas for direct user respiration.

Figure 2:
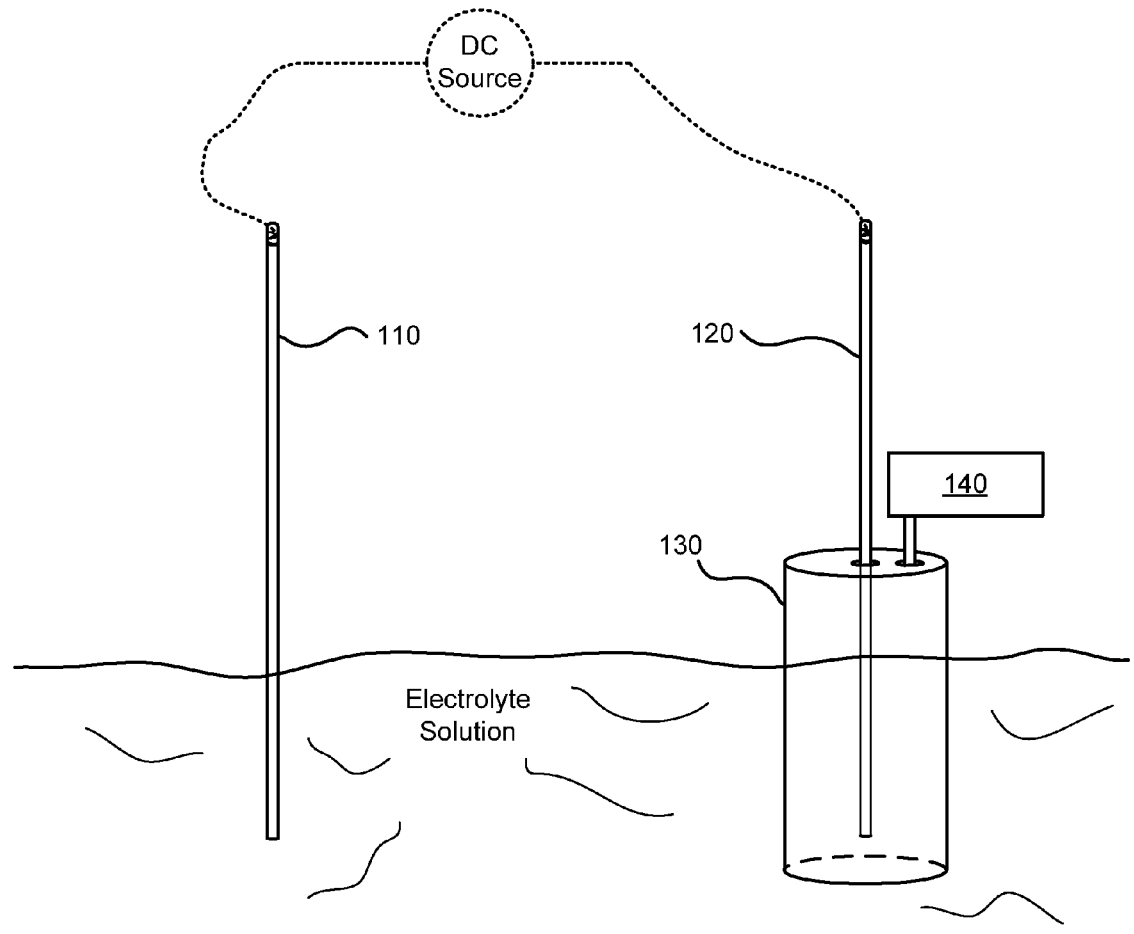
FIG. 2 depicts an electrolysis apparatus that includes an anode, a cathode, a hydrogen collector receptacle and a delivery device, according to one embodiment.

FIG. 2 depicts an electrolysis apparatus that includes an anode 110, a cathode 120, a hydrogen collector receptacle 130 and a delivery device 140, according to one embodiment. The hydrogen collector receptacle 130, in one embodiment, substantially surrounds and circumscribes the cathode 120 and includes various components for collecting and transferring hydrogen gas. The hydrogen collector receptacle 130 captures the hydrogen gas that is produced via the reduction reactions, directs the hydrogen gas upwards in a confined volume and transfers the hydrogen gas to the delivery device 140 for use in a certain application, such as direct respiration, storage, etc. The hydrogen collector receptacle 130 limits the generation and collection of hydrogen at the cathode to a specific amount.

Generally, the delivery device 140 receives collected hydrogen gas from the hydrogen collector receptacle 130 and delivers the hydrogen to a specific end-use. Thus, the delivery device 140 in FIG. 4 is shown as merely box in order to show the functionality and arrangement of the various components and is not intended to be an actual representation of any physical delivery device. In other words, the depicted delivery device 140 is a schematic block diagram that represents the general interconnectivity of the hydrogen collector receptacle 130 and the delivery device 140. Multiple specific embodiments of delivery devices that are discussed in greater detail below with reference to FIGS. 7A and 7B. Also, additional details regarding the hydrogen collector receptacle 130 are included below with reference to FIG. 3.

Figure 3:
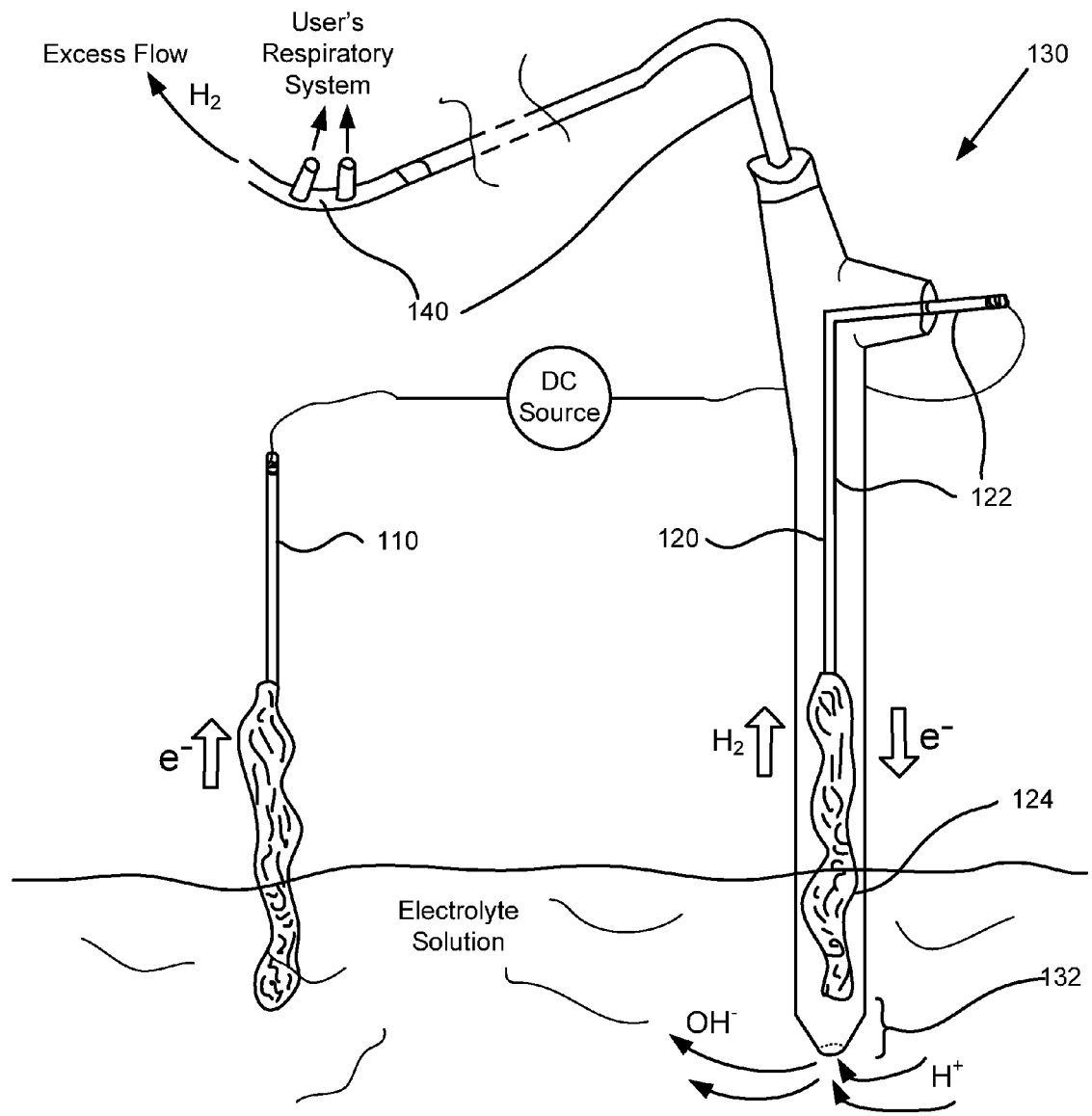
FIG. 3 depicts one embodiment of the electrolysis apparatus of FIG. 2.
Figure 4:
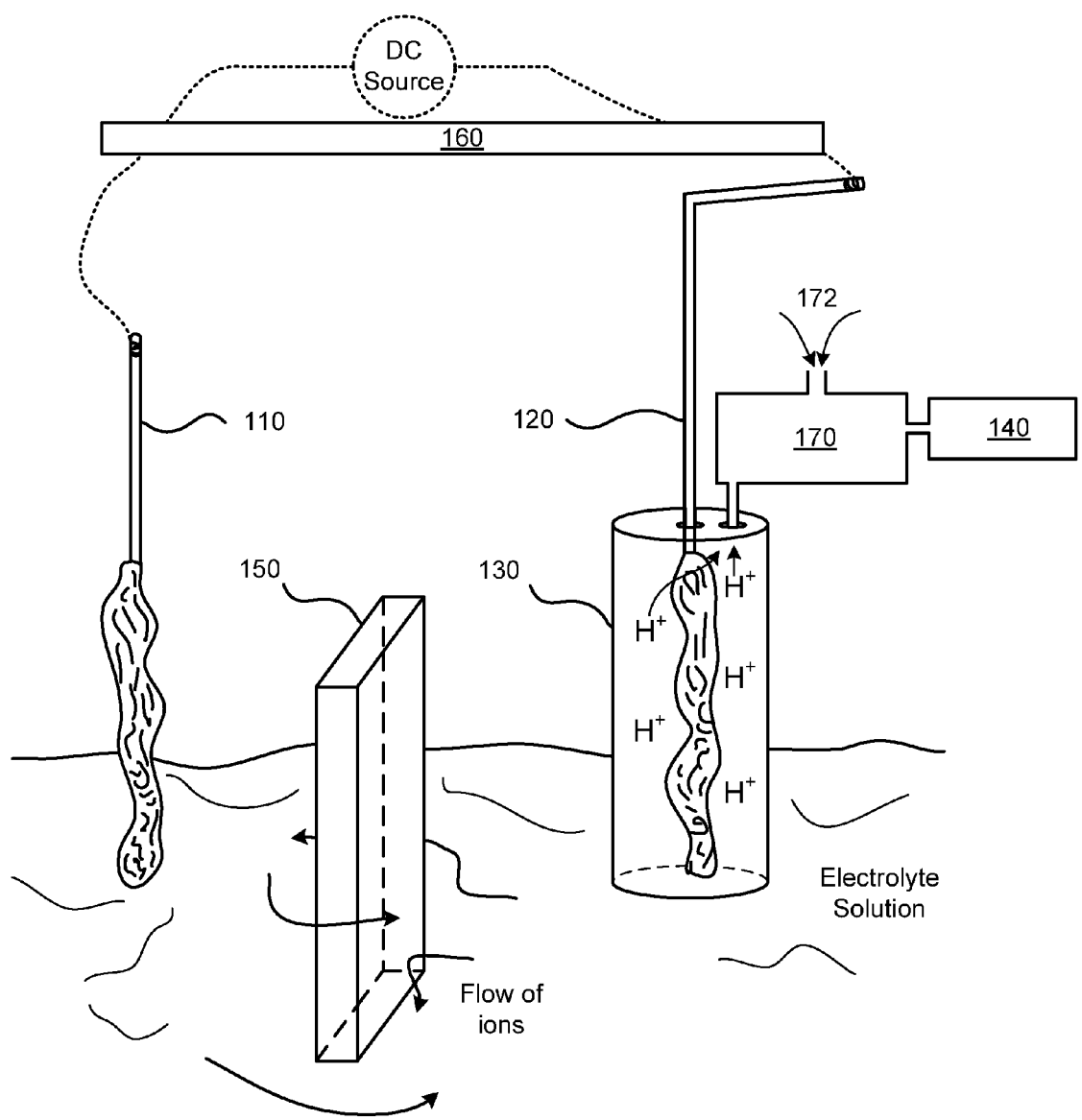
FIG. 4 depicts another electrolysis apparatus that includes an anode, a cathode, a hydrogen collector receptacle, a delivery device, an ion flow limiter, an electric control module, and a flow chamber, according to one embodiment.

FIG. 3 depicts one embodiment of the electrolysis apparatus of FIG. 2. As depicted in FIG. 3 and according to one embodiment, the electrodes 110, 120 may include a metallic mesh portion. For example, a metallic mesh typically includes more metallic surface area to react with the electrolyte. In another embodiment, the electrodes may include different shapes, sizes and orientations. For example, the anode 110 may be configured as a cylindrical rod with a distal mesh portion while the cathode 120 may be configured as a square (cross-section) rod with no mesh portion. In another embodiment, the anode 110 is substantially straight and/or the cathode 120 is substantially crooked or undulating. Thus, regardless of whether the shape, size, orientation of one of the electrodes is different than the other, the electrodes 110, 120 generally include any metallic material that is at least minimally conductive. Electrodes of various shapes may offer different amounts of surface area to react with the electrolyte. Also, the cathode 120 may have a proximal segment 122 and a distal segment 124. The proximal segment 122 is generally the portion to which the electric wires attach and the portion that is above the level of the electrolyte solution and the distal segment 124 is generally the portion that is in fluid contact with the electrolyte solution.

The hydrogen collector receptacle 130, in one embodiment, includes a tube that substantially encompasses at least the distal segment 124 of the cathode 120. Although depicted as a cylindrical chamber in both FIGS. 2 and 3, it is contemplated that the hydrogen collector receptacle 130 may have a rectangular cross-section or may be have other shapes and configurations. For example, according to one embodiment the hydrogen collector receptacle 130 may be configured to substantially contour the shape of the cathode 120. Thus, if the cathode 120 was a rectangular metal plate or a rectangular segment of metallic mesh, the hydrogen collector receptacle 130 may also have a similar shape. The hydrogen collector receptacle 130 may be constructed of a translucent or transparent material that allows a user to view the condition of the contained cathode 120. For example, in one embodiment the surface of the cathode 120 may corrode and become plated with unwanted/deposited layers, thus negatively affecting the reduction rate and/or a user's control over the reduction rate. In another embodiment, the hydrogen collector receptacle 130 is made of a plastic, ceramic, or polymer material that is capable of durably withstanding the reduction reactions at the cathode 120. In yet another embodiment, the hydrogen collector receptacle 130 is constructed of a galvanized metal that is capable of withstanding the reduction reactions at the cathode 120 and the general chemistry of the electrolyte.

At least a portion of the distal section of the hydrogen collector receptacle 130 is in fluid contact with the electrolyte solution. The hydrogen collector receptacle 130, in one embodiment, includes an aperture 132 at its distal end (near the distal segment 124 of the cathode 120). As depicted in FIG. 3, the aperture 132 may have a fixed cross-sectional area or the aperture may be configured to have a specific shape, according to the specifics of a given application. For example, in a system without the hydrogen collector receptacle 130, a current would flow from the cathode 120 into the electrolyte solution and back up through the anode 110 and a certain flow rate and concentration of cat ions and anions would exist in the system. However, if a hydrogen collector receptacle 130 with an aperture 132 is implemented in the same system, the ion flux (ion flow rate per unit area) may be altered.

Figure 7A:
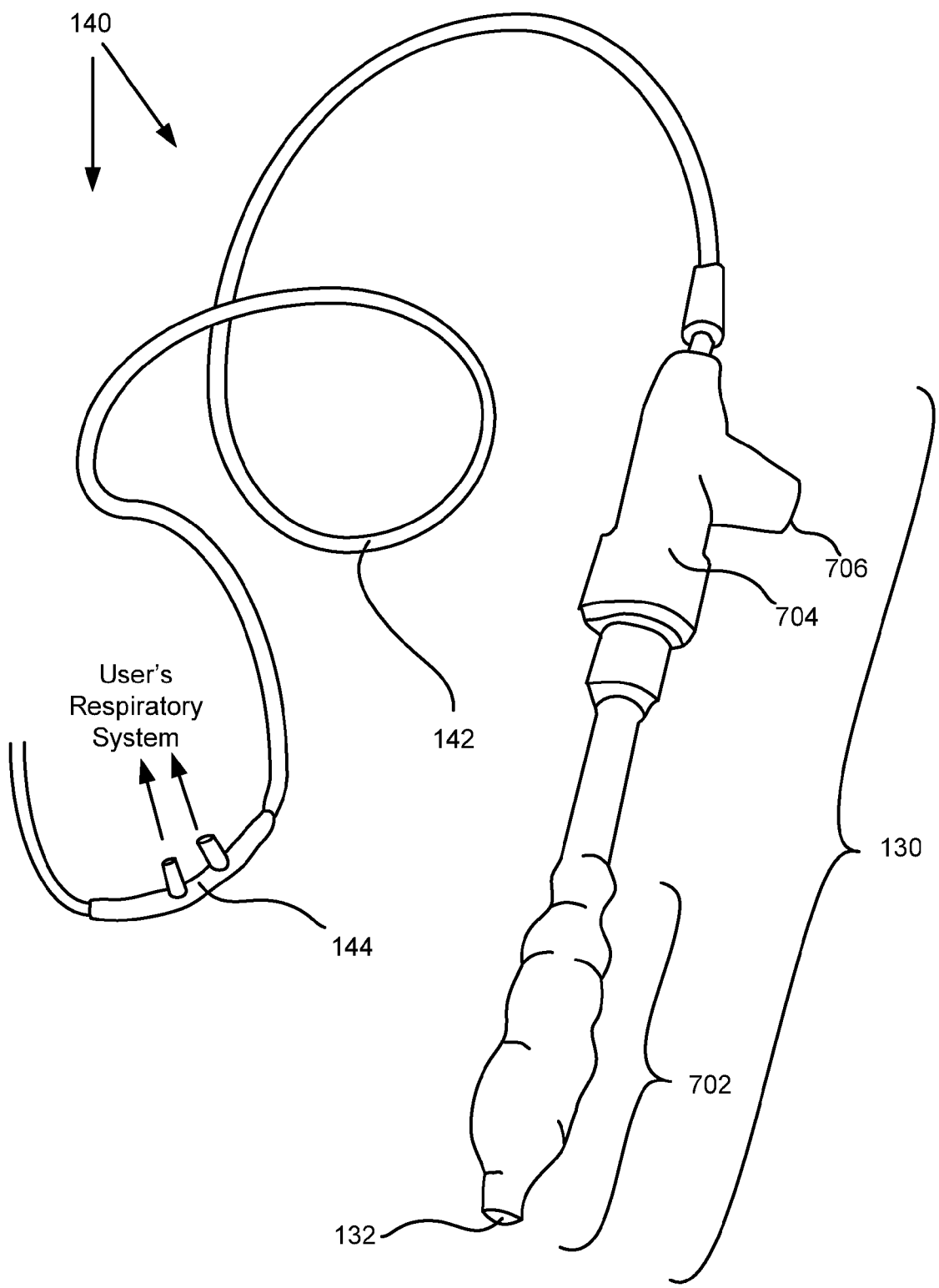
FIG. 7A depicts one embodiment of hydrogen collector receptacle and a delivery device.
Figure 7B:
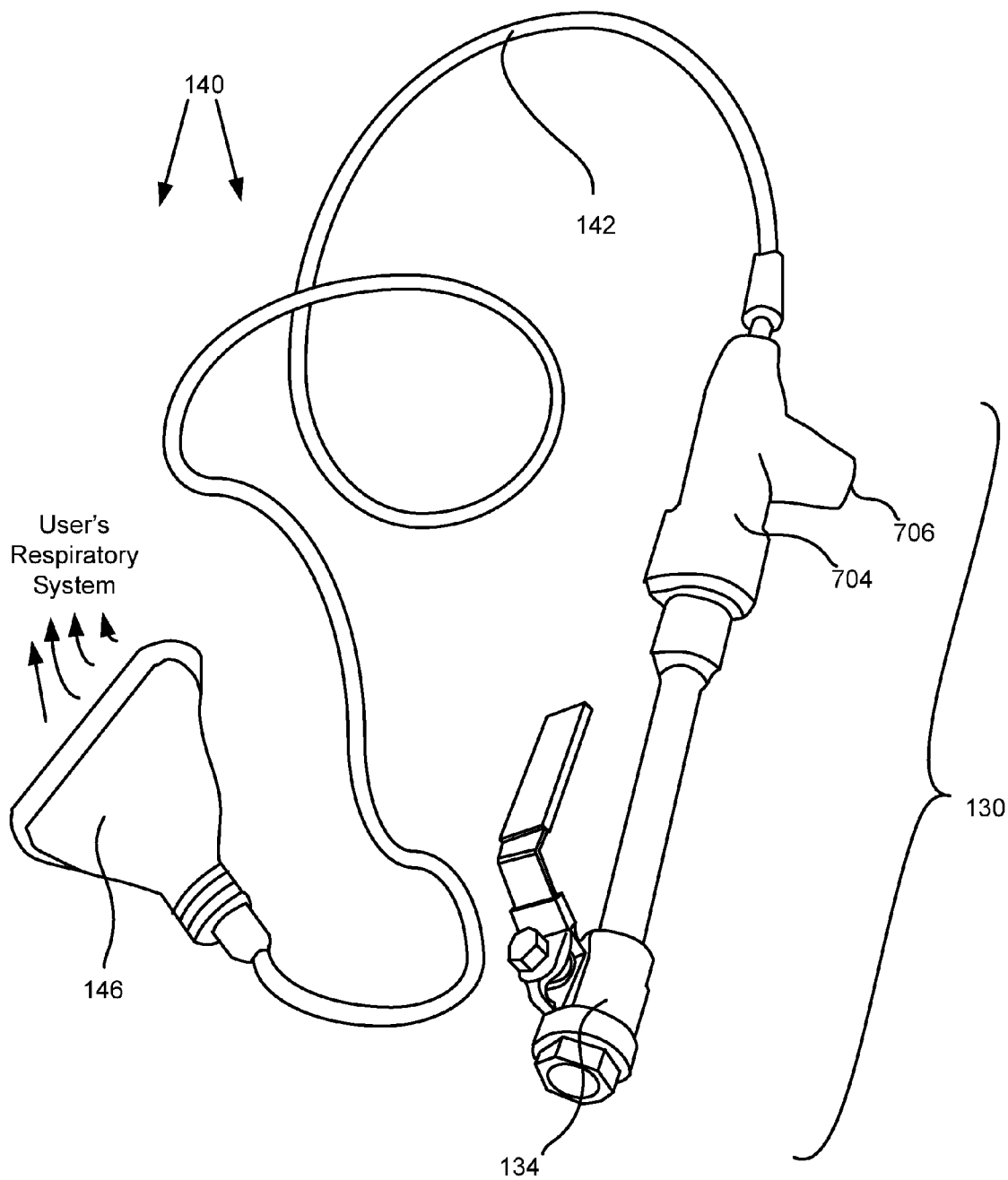
FIG. 7B depicts another embodiment of a hydrogen collector receptacle and a delivery device.

In other embodiments, as depicted in FIG. 7B, the aperture 132 may actually comprise a valve structure and the cross-sectional area of the aperture 132 may be controllably adjusted. The aperture 132 functions to limit the flow of ions to and from the cathode 120, thus contributing to controlling the rate of reduction. As depicted in FIG. 3, the hydrogen ions are attracted to and flow towards the negatively charged cathode 120 and the hydroxide ions are repelled from and flow away from the negatively charged cathode 120. Depending on the cross-sectional area of the aperture 132, more or less ions will be transferred back and forth, thus limiting/controlling the rate of electrolysis.

The depicted apparatus also includes a delivery device 140 for transferring the collected hydrogen to a specific application. For example, in one embodiment, the electrolysis apparatus of the present disclosure is directed towards a personal breathing apparatus that directly delivers hydrogen gas to a user's respiratory system. In one embodiment, the apparatus is configured to generate and collect an amount of hydrogen gas in the range of between about 0.1% and 4.5% of a user's breath. In another embodiment, the amount of hydrogen gas generated and collected is in the range of between about 1.0% and 4.0% of a user's breath. In yet another embodiment, the amount of hydrogen gas generated and collected is about 3.5% of a user's breath. Since hydrogen is flammable and has a lower flammability limit at just over 4%, it is essential, in one embodiment, for the hydrogen collector receptacle 130 to accurately control the generation and collection of hydrogen gas.

In one embodiment, the only controllable variable may be the configuration of the hydrogen collector receptacle 130 about the cathode 120. For example, depending in part on the reactive surface area of the cathode that is in fluid contact with the electrolyte solution, the configuration of the hydrogen collector receptacle 130 greatly affects both the generation rate and/or collection rate of hydrogen gas. For example, the aperture 132 in the hydrogen collector receptacle 130 may be small enough to physically limit the flow of ions to and from the cathode, thus limiting the rate of electrolysis and the subsequent generation rate of hydrogen gas. Further, the hydrogen collector receptacle 130 may be configured to have an aperture partially above (not depicted) the distal segment 124 of the cathode 120 and, based on the aperture 132, the amount of hydrogen gas collected may be limited (excess hydrogen generated but not collected may be vented to the atmosphere or transferred and collected for other uses).

In another embodiment, however, the configuration of the hydrogen collector receptacle 130 is not the only manipulated/controllable variable and other components and modules may be added to the apparatus to accurately control the generation, collection, or delivery of the proper amount of hydrogen. These other components are described below in greater detail.

FIG. 4 depicts an electrolysis apparatus that includes an anode 110, a cathode 120, a hydrogen collector receptacle 130, a delivery device 140, an ion flow limiter 150, an electric control module 160, and a flow chamber 170, according to one embodiment. While the ion flow limiter 150, the electric control module 160, and flow chamber 170 are depicted as separate from the hydrogen collector receptacle 130, the hydrogen collector receptacle 130 controls hydrogen generation and collection and may include the ion flow limiter 150, the electric control module 160, and flow chamber 170. In the depicted embodiment, electric control module 160, the flow chamber 170, and the delivery device 140 are shown as schematic blocks to merely show the interconnectivity of the various components and the general functionality of the apparatus. Additional details relating to the flow chamber 170 are included below with reference to FIGS. 6A-6C. Also, while the ion flow limiter 150 is depicted as a rectangular wall positioned between the two electrodes, additional details and embodiments of the ion flow limiter 150 are included below with reference to FIG. 5. The electric control module 160 may be a voltage controller or a current controller that interacts with the source of electricity. The current and voltage directly affects the electrolysis rate and the generation rate of hydrogen. Thus, by controlling the electricity, a user may select a desired generation rate of gaseous products.

Figure 5:
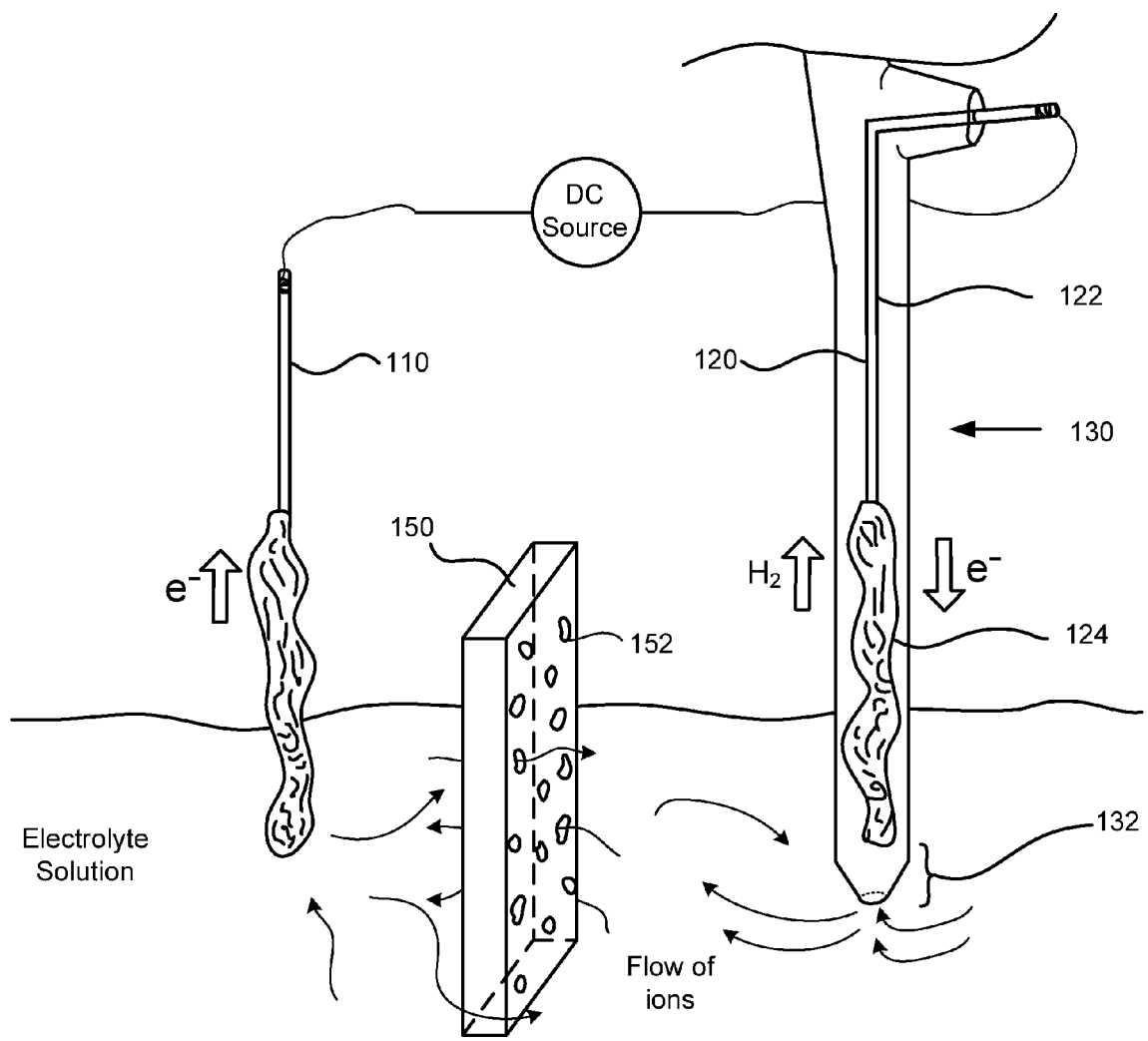
FIG. 5 depicts one embodiment of an anode, a cathode, a hydrogen collector receptacle, and an ion flow limiter.

FIG. 5 depicts one embodiment of an anode 110, a cathode 120, a hydrogen collector receptacle 130, and an ion flow limiter 150. As briefly described above in relation to the aperture 132 of the hydrogen collector receptacle 130, restricting the flow pathway of the ions can affect the rate of electrolysis and thus the generation rate of hydrogen. In some embodiments, the apparatus of the present disclosure may include an ion flow limiter 150 that further limits and/or restricts the pathway between the electrodes. As depicted in FIGS. 4 and 5, the ion flow limiter 150 can alter the direct path of the ions to and from the cathode 120 and the anode 110. In one embodiment (FIG. 4), the flow limiter 150 may be a solid separating wall that forces ions to flow around it in order to reach the destination electrode. In another embodiment (FIG. 5), the ion flow limiter 150 may have perforations throughout its body, thus restricting the flow of ions that can directly transfer back and forth between the electrodes.

In yet another embodiment (not depicted), the ion flow limiter 150 may include multiple plates that can be variably positioned and configured to increase or decrease the rate of electrolysis. For example, two perforated plates may be movably juxtaposed together and, depending on the degree to which the perforations in the two plates align, the cross-sectional flow area directly between the two electrodes may be controlled. It is contemplated that other components or configurations may be employed to controllably limit the rate of electrolysis and that such other components and configurations fall within the scope of the present disclosure.

Figure 6A:
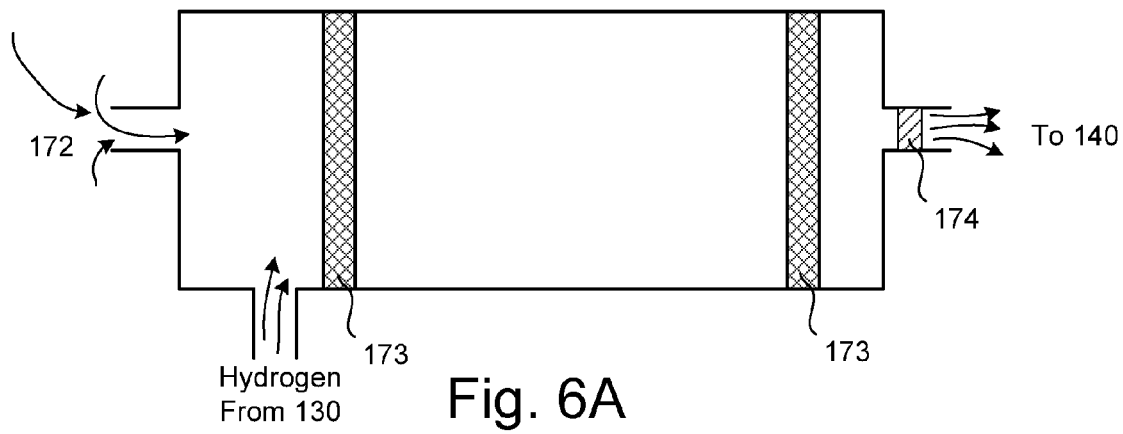
FIG. 6A depicts one embodiment of a flow chamber.
Figure 6B:
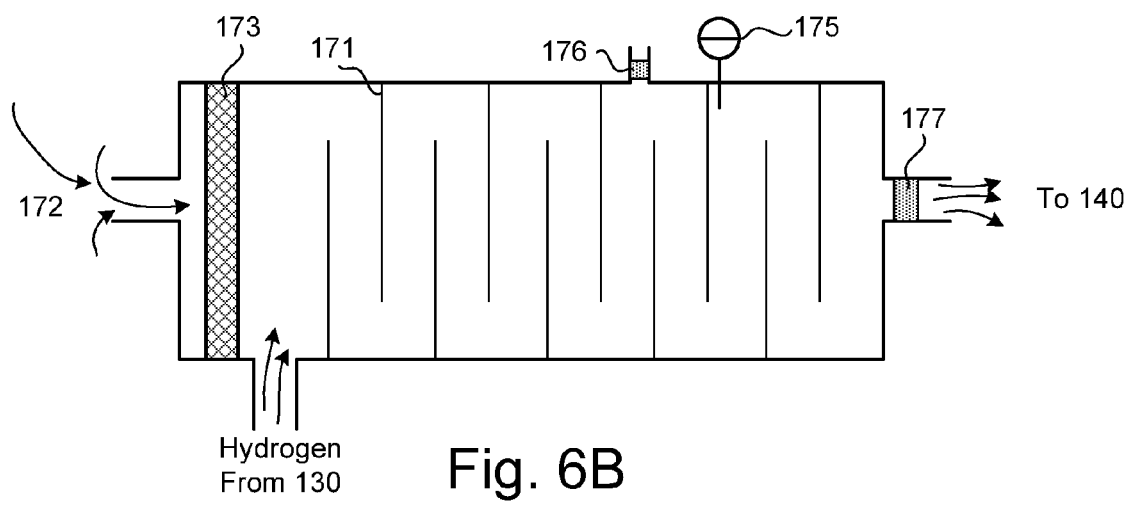
FIG. 6B depicts another embodiment of a flow chamber.
Figure 6C:
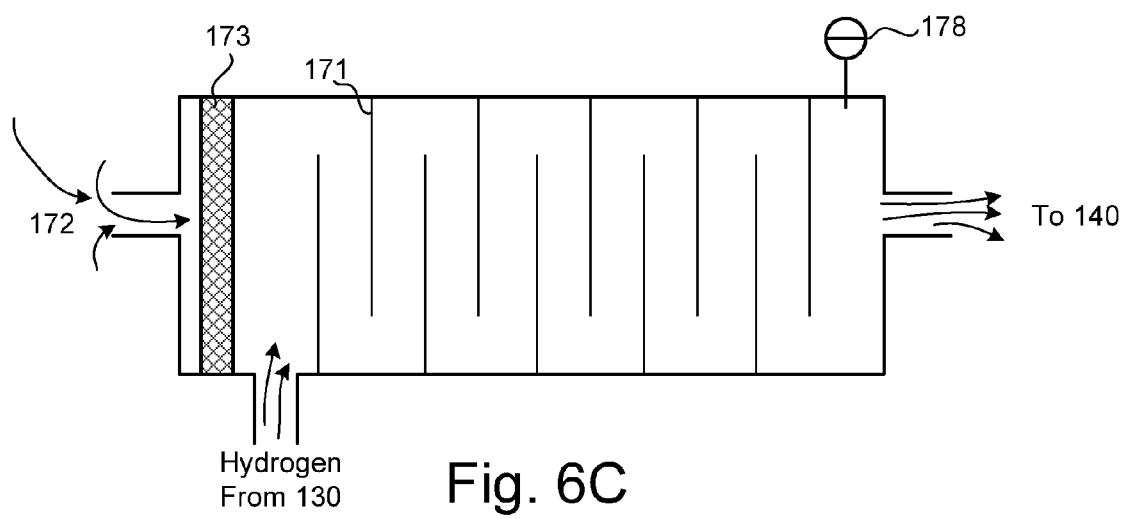
FIG. 6C depicts yet another embodiment of a flow chamber.

FIGS. 6A-6C depict various embodiments of flow chambers 170 that can be used in the present disclosure. Once again, the shape of the flow chamber as a box is not intended to be a physical limitation or an actual representation of a practicing embodiment. Rather, the depicted flow chambers 170 are schematic diagrams that show how various components can be implemented to control the delivery of the proper concentration of hydrogen to the delivery device 140. Thus, the flow chamber 170 may be a section of tubing or a portion of piping. In another embodiment, the flow chamber 170 may be a unit coupled to the hydrogen collector receptacle 130. Generally, the flow chamber 170 prepares the collected hydrogen for use in the delivery device 140. For example, such preparation may include mixing the hydrogen with a delivery fluid 172 to dilute the hydrogen to a safe level, heating or cooling the hydrogen to a proper temperature, increasing or decreasing the pressure within the flow chamber 170, and venting excess hydrogen to the atmosphere or to another end-use (storage), among others. The delivery fluid 172 may be air, according to one embodiment. However, it is contemplated that other delivery fluids 172, depending on the specifics of a given application, may be used (e.g., pure oxygen).

FIG. 6A depicts one embodiment of a flow chamber 170 of the present disclosure. In the depicted embodiment, the flow chamber 170 includes two fans/compressors 173 and a flow sensor 174. Depending on the flow rate (velocity, volumetric flow rate, mass flow rate), the fans/compressors 173 may be controlled to increase or decrease the pressure within the chamber 170. For example, if a controller (not depicted) determines that, based on the flow rate detected at the flow sensor 174, too much hydrogen will be transferred to the delivery device, the controller may adjust the rate of the first fan/compressor to pull in more air and thus decrease the relative concentration of hydrogen in the chamber 170.

FIG. 6B depicts another embodiment of a flow chamber 170 of the present disclosure. In the depicted embodiment, the flow chamber 170 includes a fan/compressor 173, mixers 171, a pressure sensor 175, a vent valve 176 and a one way valve 177. Based on the pressure detected by the pressure sensor 175, the fan/compressor 173 may be controlled to increase or decrease the pressure within the chamber 170. In another embodiment, the vent valve 176 may also be opened to vent a portion of the hydrogen and delivery fluid 172 so as to decrease the pressure within the chamber. The one way valve 177 may be configured so that, as a user inhales through a nasal respirator attached to the one way valve 177, the valve opens to allow an intake of hydrogen and air from the chamber 170. The mixer 171 depicted is a plurality of vanes or fins that extend into the chamber from the chamber walls. The fan 173 blows the air and hydrogen through the tortuous pathway created by the fins to promote the mixture of air and hydrogen. It is contemplated that other mixers, such as fan blades, may also be implemented to promote mixing the two fluids together.

FIG. 6C depicts yet another embodiment of a flow chamber 170 of the present disclosure. In the depicted embodiment, the flow chamber 170 includes a fan/compressor 173 and a hydrogen sensor 178. The hydrogen sensor 178 may detect the amount of hydrogen that is present in the chamber and the fan/compressor 173 may be actuated to increase or decrease the inlet flow of air to the chamber to adjust the composition of the fluid mixture. FIGS. 6A-6C are illustrative of the various components that can be implemented to control the dilution of hydrogen with a delivery fluid 172. It is contemplated that the listed components, as well as other components not listed such as additional valves, fittings, mixers, compressors, fans, may be used in various configurations and combinations to create a flow chamber 170 that receives hydrogen from the collector receptacle 130 and controllably mixes and transfers a desired concentration of hydrogen to the delivery device 140. In one embodiment, the flow chamber 170 may be passive and the inhalation from a user triggers the transfer of hydrogen from the flow chamber 170 to the delivery device 140. For example, upon inhalation a user may create a vacuum in the delivery device 140 that causes a valve or a venture-type orifice to actuate, thereby causing the mixture of hydrogen and the delivery fluid 172 to exit the flow chamber 170 and enter the delivery device 140.

FIG. 7A depicts one embodiment of a hydrogen collector receptacle 130 and a delivery device 140. For clarity in illustrating the various components of the hydrogen collector receptacle 130 and the delivery device 140, the cathode 120 contained within the hydrogen collector receptacle 130 is not depicted in FIG. 7A. The hydrogen collector receptacle 130 depicted in FIG. 7A comprises a tube that is shaped according to the undulating nature of a metallic mesh cathode 120 (not depicted). In one embodiment, this undulating portion 702 of the hydrogen collector receptacle 130 is a glass bulb that contours the cathode 120 contained within (not depicted).

The collector receptacle 130 may also include a proximal housing section 704 that couples with the delivery device 140. The housing section 704 may include a sealable aperture or fastening means 706 for electrically connecting the cathode 120 to an electrical energy source. The collector tube 130, in one embodiment, also includes an attachment means for connecting the delivery device 140 to the collector receptacle 130. The hydrogen collector receptacle 130 also includes an aperture 132. Generally the aperture 132 is a component of the distal portion 702 of the collector receptacle 130. As described briefly above and according to one embodiment, the distal segment 122 of the cathode 120 and the distal portion 702 of the hydrogen collector receptacle 130 are in fluid contact with the electrolyte solution in order for the apparatus to perform according to the disclosure contained herein.

The hydrogen collector receptacle 130 is attached to a delivery device 140. Generally, the delivery device 140 attaches to the proximal housing section 704 of the collector receptacle 130. As depicted, the delivery device 140 may include plastic tubing 142 and a nasal cannula 144 for directly transferring hydrogen to a user's respiratory system. The tubing may be plastic, rubber, or other suitable material. As described above, the hydrogen collector receptacle 130 may be configured so that a certain volumetric percentage of each breath comprises hydrogen gas. In one embodiment the gas delivery device 140 may also include an open-ended portion that allows for excess fluid that has not been taken into the respiratory system by the user to flow harmlessly out of the delivery device 140. In one embodiment, although not depicted, a flow chamber 170 may be inserted between the plastic tubing 142 and the housing section 704 of the collector receptacle 130.

FIG. 7B depicts another embodiment of a hydrogen collector receptacle 130 and a delivery device 140. For clarity in illustrating the various components of the hydrogen collector receptacle 130, the cathode 120 contained within the hydrogen collector receptacle 130 is not depicted in FIG. 7B. FIG. 3B illustrates a hydrogen collector receptacle 130 that includes a valve 134 as the aperture 132. The valve 134 may create an aperture that extends beyond the distal tip of the cathode 120. For example, the valve 134 may be controlled by a user or a controller to create different sized openings at the distal tip of the collector receptacle 130, thus manipulating the ion flow rates to and from the cathode 120 and allowing for greater control in the generation rate of hydrogen gas.

In one embodiment, the valve 134 may require manually adjusting the position of the valve handle in order to manipulate the control surface of the valve 134 to create an aperture of specific size. In another embodiment, the valve 134 may be configured with a controller to automatically control the position of the control surface of the valve 134. In one embodiment, hydrogen collector receptacle 130 may include means for sensing the concentration and/or flow rate of hydrogen gas and for communicating the sensed levels to the controller. The controller may then adjust the valve 134 accordingly to bring the measured level of hydrogen gas generation closer to the anticipated or set value.

As described above with reference to FIG. 7A, the various components of the hydrogen collector receptacle 130 may be constructed of different materials. For example, the valve 134 may be constructed of a galvanized metal, a plastic, a ceramic, a polymer material, or some other material recognized by those of skill in the art as capable of being used in an electrolysis system. If the valve 134 was metal but was not galvanized, the metallic material of the valve may corrode and decompose during electrolysis.

The depicted embodiment also includes a delivery device 140 that includes plastic tubing 142 and a respirator mask 146 for covering a user's mouth and nostrils to deliver hydrogen gas to the respiratory system. In one embodiment (not depicted), the delivery device 140 may simply include a tube that may be position in proximity to the end-use application (e.g. a user's mouth and/or nose). It is contemplated that other types of delivery devices 140 may be used in accordance with the present invention. For example, the delivery device 140 may include pipes directing the hydrogen gas to a storage container.

The embodiments of the hydrogen collector receptacle 130 as depicted in FIGS. 7A and 7B are exemplary and are not intended as an exhaustive depiction of all the embodiments. For example, various components from one depicted embodiment may be combined in a different way with components from another depicted embodiment. It is also contemplated that one of ordinary level of skill in the art may recognize additional implementations or variations of the various components described in the present disclosure and such additional implementations fall within the scope of the present disclosure.

Figure 8:
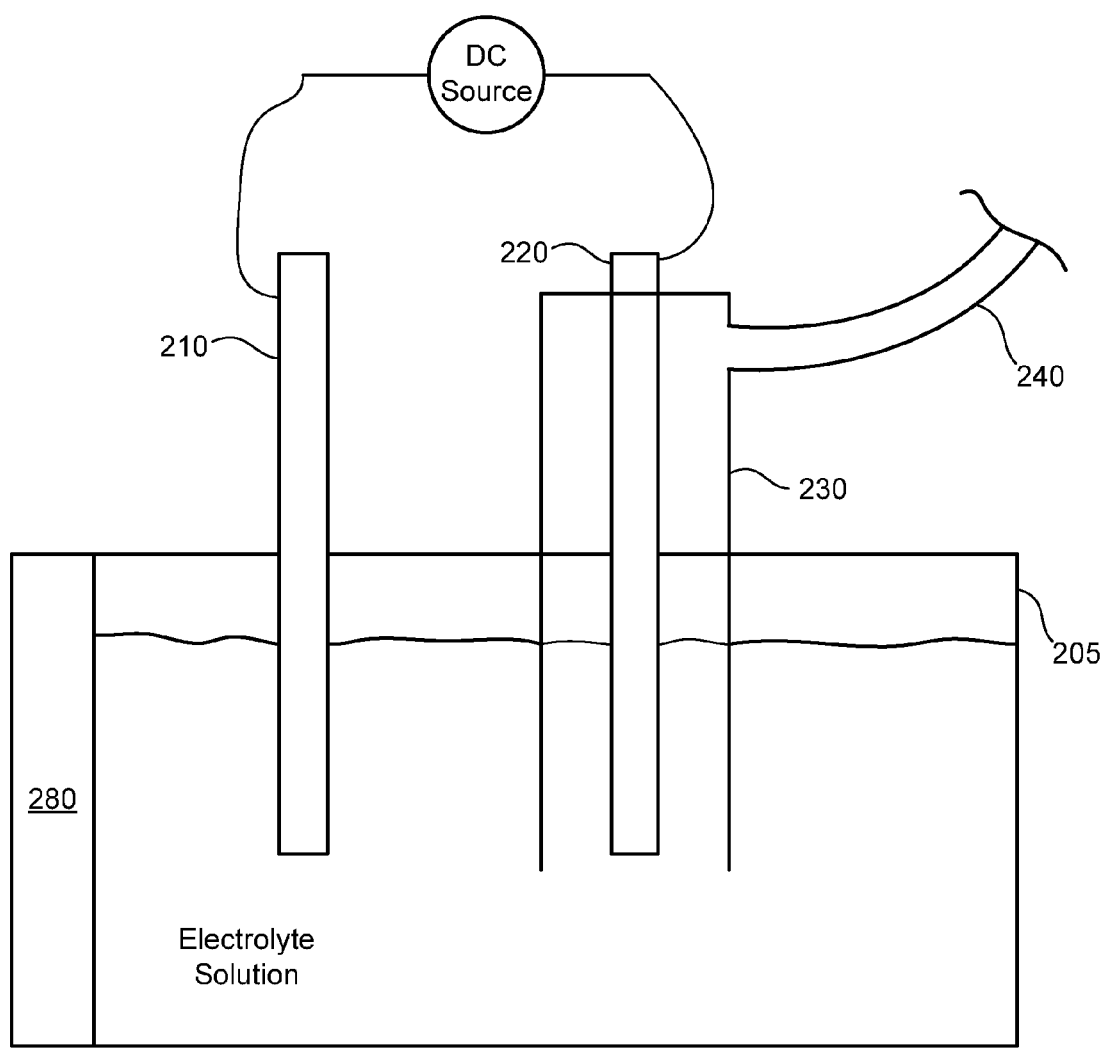
FIG. 8 depicts an electrolysis system that includes an electrolyte vessel, an anode, a cathode, a hydrogen collector receptacle, and a delivery device, according to one embodiment.
Figure 9:
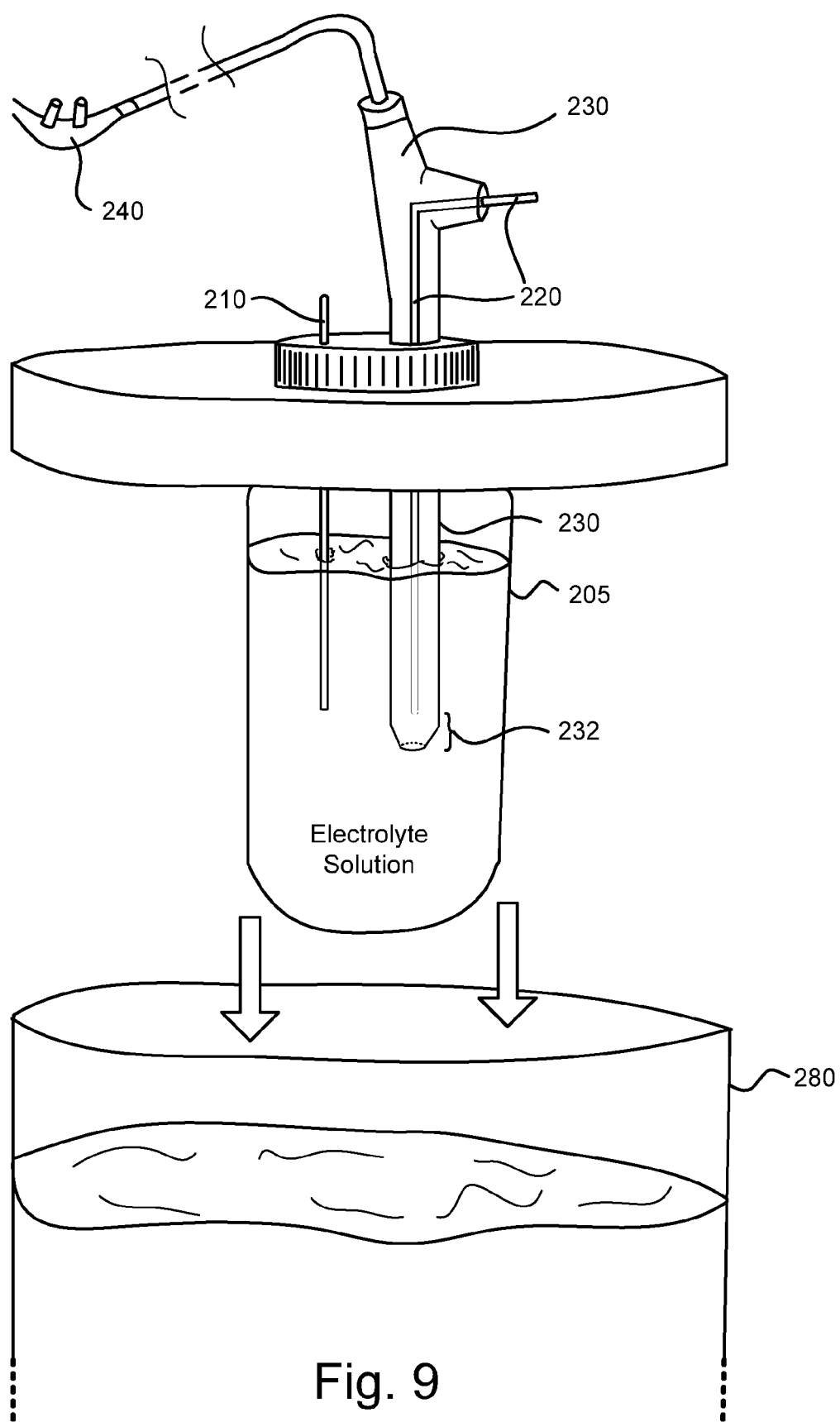
FIG. 9 depicts an electrolysis system that includes an electrolyte vessel, an anode, a cathode, a hydrogen collector receptacle, a delivery device, and an electrolyte temperature control module, according to one embodiment.

FIG. 8 depicts an electrolysis system that includes an electrolyte vessel 205, an anode 210, a cathode 220, a hydrogen collector receptacle 230, a delivery device 240, and an electrolyte temperature control module 280, according to one embodiment. The electrolyte vessel 205 and the electrolyte temperature control module 280 are described below with reference to FIG. 9 and the other components depicted in the system have been previously described above. FIG. 9 is not an actual depiction of a physical system, but rather is a schematic diagram showing one embodiment of the interconnectivity of the various components.

FIG. 9 depicts one embodiment of an electrolysis system for collecting hydrogen gas in accordance with the present disclosure. The electrolysis system, in one embodiment, includes an anode 210 and a cathode 220, a hydrogen collector receptacle 230, an electrolyte vessel 205, and an electrolyte temperature control module 280. In the embodiment depicted in FIG. 9, the electrolyte vessel 205 and the electrolyte temperature control module 280 are removed a distance from each other in order to clearly illustrate the various components of the apparatus. Also for clarity, the hydrogen collector receptacle 230, the electrolyte vessel 205, and the electrolyte temperature control module 280 are depicted as transparent (i.e. glass) in order to show the components contained therein. FIG. 9 also depicts an electrolyte solution.

Figure 10:
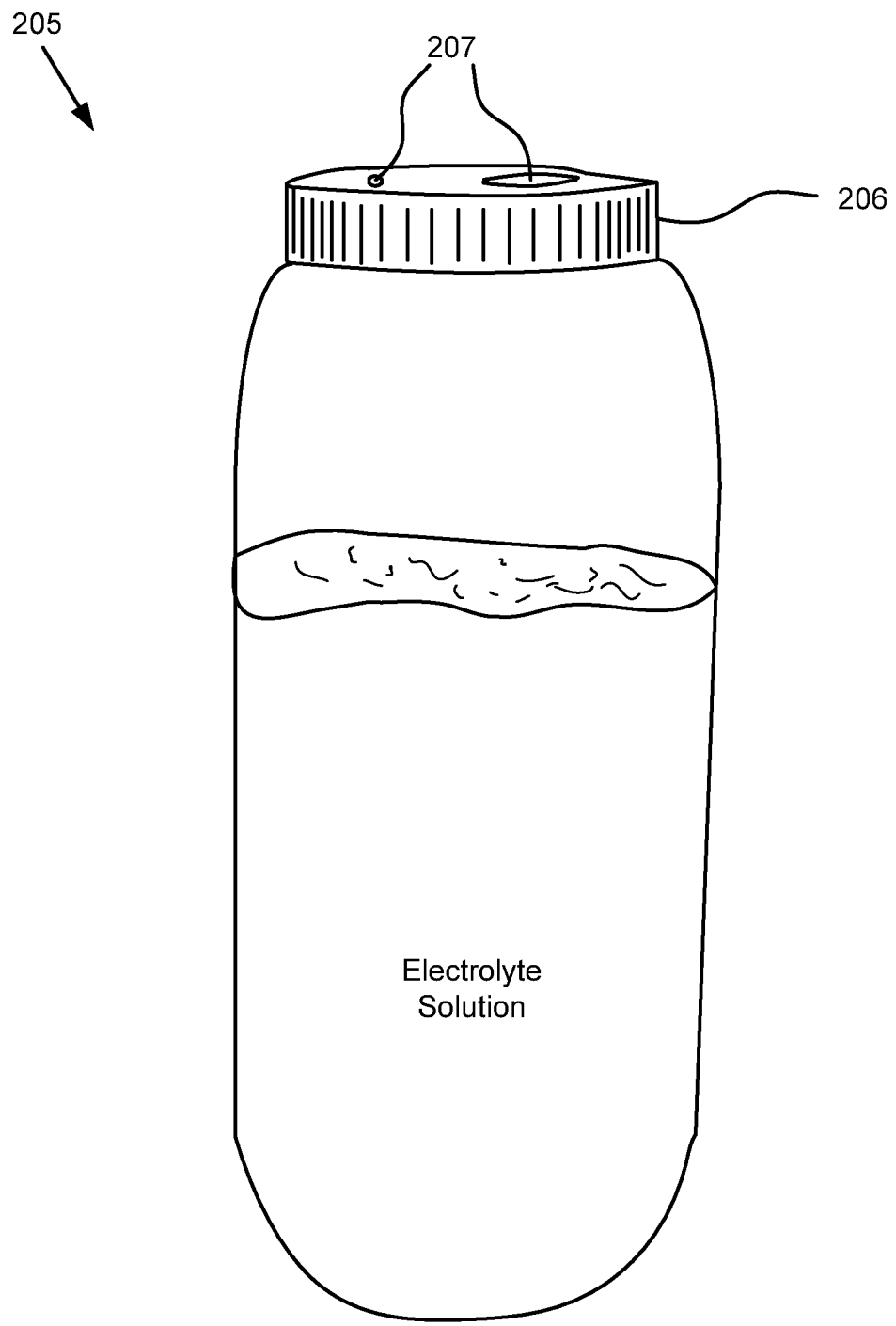
FIG. 10 depicts an electrolyte vessel, according to one embodiment.

FIG. 10 depicts an electrolyte vessel, according to one embodiment. The electrolyte vessel 205 may be a glass, plastic, polymer, ceramic, or galvanized metallic material. Depending on the specifics of a given application, the electrolyte vessel 205 may be sized to hold various volumes of electrolyte solution. For example, if the electrolysis system disclosed herein were to be implemented as a personal hydrogen respiration device for a single user, the electrolyte vessel 205 may only need to hold several quarts of electrolyte solution. In another embodiment, where the electrolysis system of the present disclosure is implemented to generate, collect and deliver hydrogen to several different sources and/or several different users, the electrolyte vessel 205 may be sized to hold substantially more electrolyte solution.

The electrolyte vessel 205 may also include two separate chambers that are connected with a salt bridge (similar to a galvanic cell configuration). In such embodiments, specific electrolyte solution may be selected based upon the type of material of each electrode (anode 110 and cathode 120). The selection of the electrolyte solution may be according to the material of the electrodes 110, 120, the end-use of the gases generated, the size and materials of the components of the apparatus system, and other factors.

The electrolyte vessel 205 may also include a removable lid 206 for enclosing the electrolyte solution within the chamber. The electrolyte vessel 205 may also include a mounting mechanism 207, for example on the lid 206, that enables the electrodes 110, 120 and/or the hydrogen collector receptacle 130 to attach to the electrolyte vessel 205 and maintain at least a portion of the electrodes 110, 120 in fluid communication with the electrolyte solution. Also, the electrolyte vessel 205 may include a vent (not depicted) that allows any pressure build-up in the chamber to be released.

Figure 11:
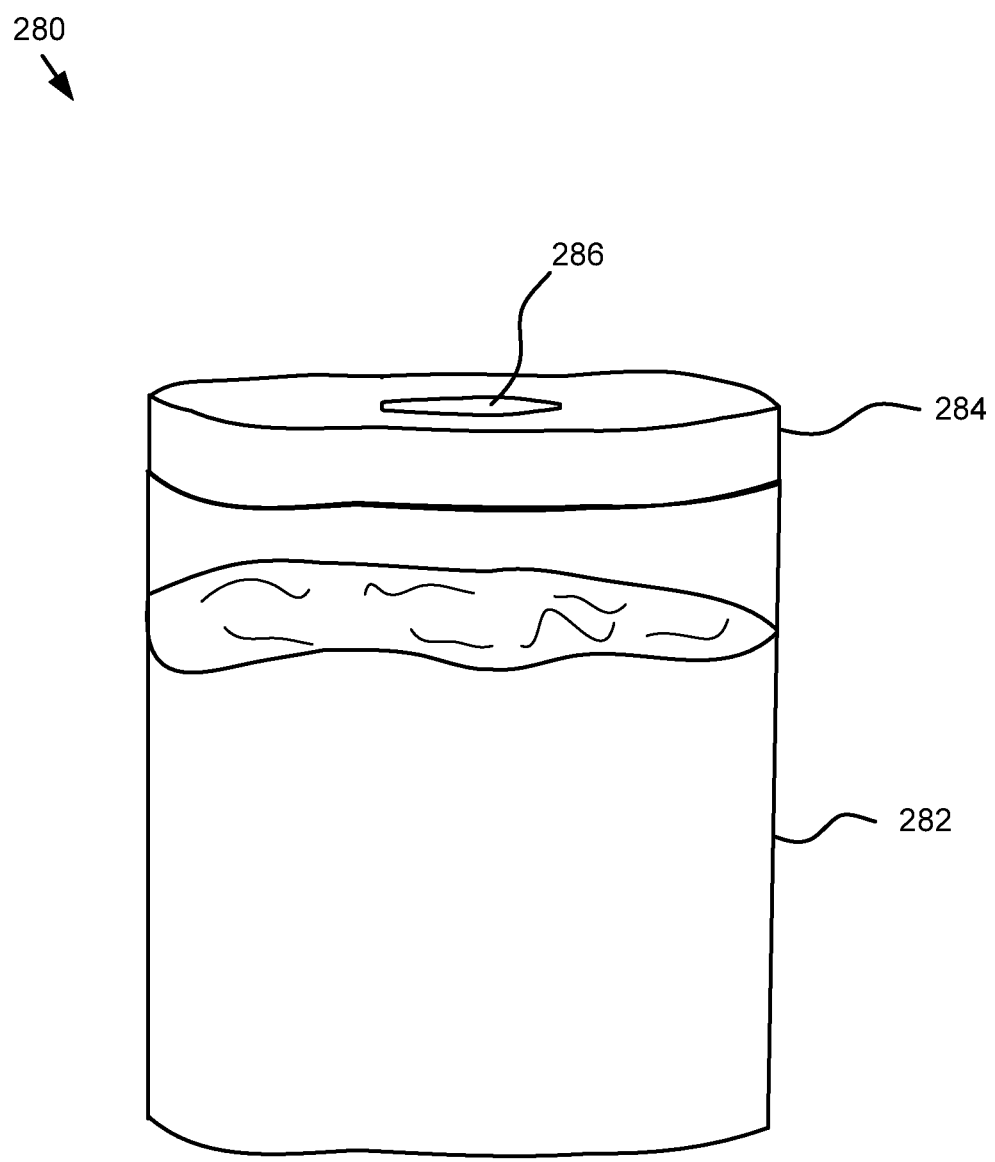
FIG. 11 depicts an electrolyte temperature control module, according to one embodiment.

FIG. 11 depicts an electrolyte temperature control module, according to one embodiment. The redox reactions involved with the electrolysis process are often exothermic and heat is generated in the electrolyte vessel 205. In order to control the temperature of the electrolyte solution in the electrolyte vessel 205, various components may be implemented that absorb or dissipate the temperature fluctuations and substantially maintain the electrolyte solution at or below a certain temperature.

In one embodiment, as depicted in FIG. 11, an outer chamber 282 filled with a heat exchange fluid may be used to control the temperature of the electrolyte solution by absorbing heat generated in the electrolyte vessel 205. Depending on the specifics of a given application, the temperatures in the electrolyte solution may rise to about 200 degrees Fahrenheit. In one embodiment, the heat exchange fluid is simply water that may be periodically emptied or that may be process-cooled using an evaporator or other cooling procedure. The outer temperature control chamber 282 may also include a lid 284 that encloses the heat exchange fluid and a second mounting mechanism 286 for mounting the electrolyte vessel 205 to the temperature control outer chamber 282. The second mounting mechanism 286 may include threads that correspond with threads on the electrolyte vessel 205. In another embodiment, the second mounting mechanism 286 may include a lip or a surface upon which a shoulder of the electrolyte vessel 205 may engage. In another embodiment, the electrolyte temperature control module 280 includes conduction, radiation, or convention heat transfer systems.

Figure 12:
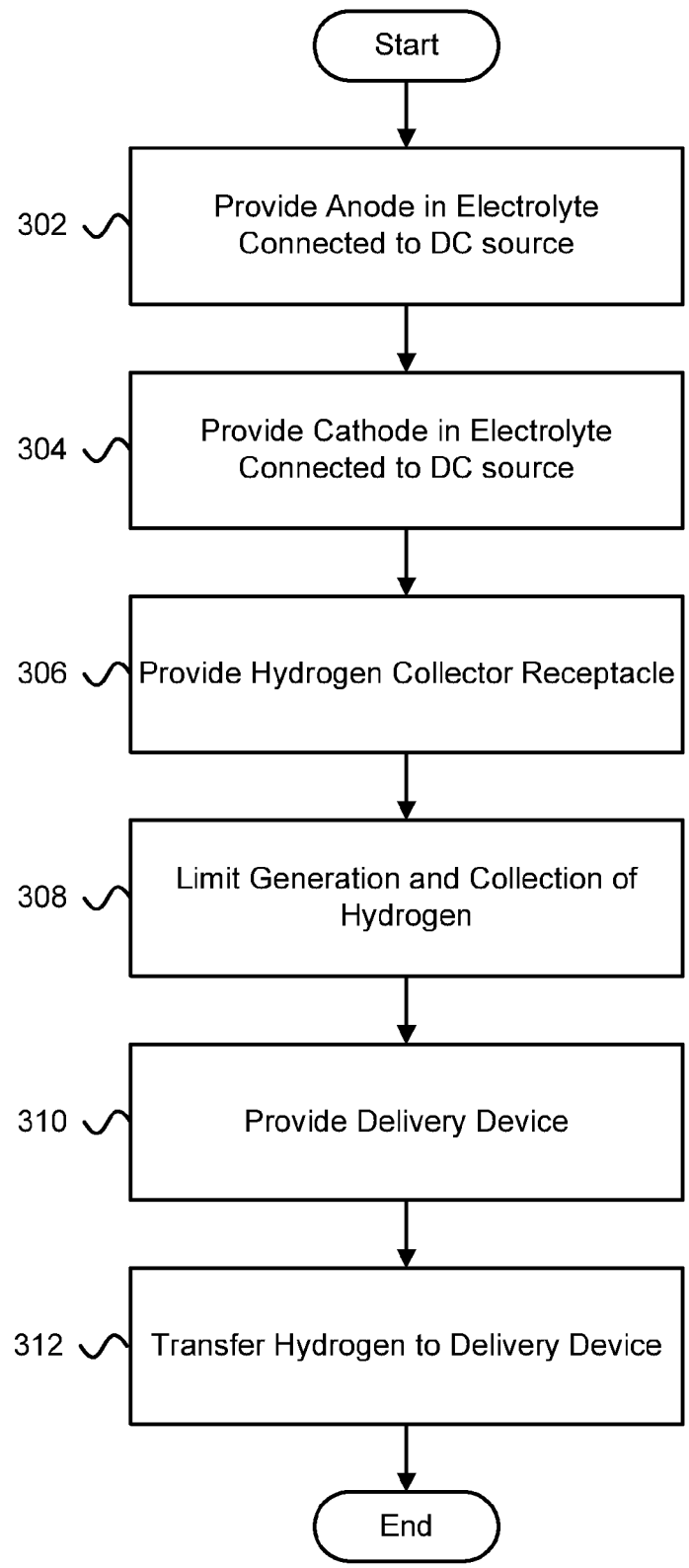
FIG. 12 is a schematic flow chart diagram of one embodiment of an electrolysis method for generating hydrogen gas.

FIG. 12 is a schematic flow chart diagram depicting one embodiment of an electrolysis method for generating hydrogen gas. The method includes providing 302 an anode 110 in fluid contact with an electrolyte solution and electrically connected to a direct current electrical source. The method also includes providing 304 a cathode 120 in fluid contact with the electrolyte solution and electrically connected to the direct current electrical source. Further, the method includes providing 306 a hydrogen collector receptacle 130 encompassing a portion of the cathode 120. The method also includes limiting 308 the generation and collection of hydrogen at the cathode 120 to a specific amount by restricting the flow of ions in the electrolyte solution to and from the cathode 120 with the hydrogen collector receptacle 130. Additionally, the method includes providing 310 a delivery device 140 that is connected to the hydrogen collector receptacle 130. Further, the method includes transferring 312 hydrogen collected in the hydrogen collector receptacle 130 to the delivery device 140.

The following example includes specific details relating to one implementation of the electrolysis apparatus and system as disclosed generally herein. A glass straw was designed from a ½ inch glass tube. A 1.3 by 3.0 inch cylindrical bulb was formed at the distal portion of the straw and a tapered aperture was formed at the distal tip of the glass straw (collector receptacle 130). A copper mesh was inserted as the cathode 120 into the bulb portion of the straw and the mesh was electrically connected to an electrical source. A stainless steel mesh was connected with the electrical source to form the anode 110.

The anode mesh 110 and the cathode mesh 120 with the surround straw were inserted into pre-formed holes in the lid 206, 207 of a glass jar. The glass jar served as the electrolyte vessel 205 and was filled with an aqueous sodium bicarbonate electrolyte solution. The electrolyte vessel 205 in the form of a glass jar was then affixed to the lid 286 of a 5 gallon plastic bucket. The plastic bucket was filled with water and served as an outer chamber 282 to absorb and control temperature of the electrolyte vessel 205 by absorbing the heat generated by the electrolysis reactions. The plastic bucket functioned as the electrolyte temperature control module 280.

Finally the straw was configured with a plastic housing section 704 above the glass jar that extended the volume of the collector receptacle 130. The plastic housing section 704 included a hole and connection means for connecting plastic tubing 142 to the collector receptacle 130. The plastic tubing 142 included a nasal cannula 144 and together the tubing 142 and the cannula 144 served as the delivery device 140. When an electric current was passed through the system, hydrogen gas was generated, collected and transferred to a user's respiratory system at 3.5% of the user's breath. Since the plastic tubing 142 was open-ended, unused hydrogen gas was simply expelled out of the open end. The interior temperature of the straw was maintained below 180 degrees Fahrenheit and the outer container maintained a water temperature of 135 degrees Fahrenheit or lower.

The subject matter of the present disclosure may be embodied in other specific forms without departing from its spirit or essential characteristics. The described embodiments are to be considered in all respects only as illustrative and not restrictive. The scope of the disclosure is, therefore, indicated by the appended claims rather than by the foregoing description. All changes which come within the meaning and range of equivalency of the claims are to be embraced within their scope.

What is claimed is:

1. An electrolysis apparatus comprising:
   an anode electrically connectable to a direct current electrical source;
   a cathode comprising a proximal segment and a distal segment, wherein the proximal segment is electrically connectable to the direct current electrical source;
   a hydrogen collector receptacle that limits generation and collection of hydrogen at the cathode to a specific amount, wherein the hydrogen collector receptacle encompasses a portion of the cathode; and
   a delivery device that receives hydrogen from and is connected to the hydrogen collector receptacle, and that delivers hydrogen gas to a user, the delivery device comprising a nasal cannula.

2. The electrolysis apparatus of claim 1, wherein the hydrogen collector receptacle circumferentially encompasses a portion of the cathode and has an aperture near the distal segment of the cathode.

3. The electrolysis apparatus of claim 2, wherein the aperture of the hydrogen collector receptacle comprises a valve that is configurable to adjust a size of the aperture for controlling a rate of electrolysis.

4. The electrolysis apparatus of claim 1, further comprising an ion flow limiter module that controls the rate of electrolysis.

5. The electrolysis apparatus of claim 4, wherein the ion flow limiter module comprises a wall between the cathode and the anode that partially restricts the flow ions between the cathode and the anode.

6. The electrolysis apparatus of claim 5, wherein the wall comprises a perforated separating wall that restricts the flow of ions between the cathode and the anode.

7. The electrolysis apparatus of claim 1, further comprising an electric control module that controls the rate of electrolysis.

8. The electrolysis apparatus of claim 1, further comprising a flow chamber interconnected between the hydrogen collector receptacle and the delivery device, wherein the flow chamber controls the transfer of hydrogen from the hydrogen collector receptacle to the delivery device.

9. The electrolysis apparatus of claim 8, wherein the flow chamber introduces and combines a delivery fluid with the collected hydrogen to control the concentration of hydrogen transferred to the delivery device, the flow chamber comprising a plurality of fins that extend into the flow chamber for mixing the hydrogen and the delivery fluid.

10. The electrolysis apparatus of claim 1, wherein at least a portion of one or more of the cathode and the anode comprises a metallic mesh.

11. The electrolysis apparatus of claim 1, wherein the cathode comprises a copper mesh.

12. The electrolysis apparatus of claim 1, wherein the anode comprises a stainless steel mesh.

13. An electrolysis system comprising:
an electrolyte vessel containing an electrolyte solution;
an anode electrically connectable to a direct current electrical source, wherein at least a portion of the anode is in fluid contact with the electrolyte solution;
a cathode comprising a proximal segment and a distal segment, wherein the proximal segment is electrically connectable to the direct current electrical source and the distal segment is in fluid contact with the electrolyte solution;
a hydrogen collector receptacle that limits generation and collection of hydrogen at the cathode to a specific amount, wherein the hydrogen collector receptacle encompasses a portion of the cathode;
a delivery device that receives hydrogen from and is connected to the hydrogen collector receptacle, and that delivers hydrogen gas to a user, the delivery device comprising a nasal cannula; and
an electrolyte temperature control module for controlling the temperature of the electrolyte.

14. The electrolysis system of claim 13, wherein the hydrogen collector receptacle circumferentially encompasses a portion of the cathode and has an aperture near the distal segment of the cathode.

15. The electrolysis system of claim 14, wherein the electrolyte temperature control module comprises an outer vessel that is configured to control the temperature of the electrolyte in the electrolyte vessel.

16. An electrolysis method for generating hydrogen comprising:
providing an anode in fluid contact with an electrolyte solution and electrically connected to a direct current electrical source;
providing a cathode in fluid contact with the electrolyte solution and electrically connected to the direct current electrical source;
providing a hydrogen collector receptacle encompassing a portion of the cathode;
limiting the generation and collection of hydrogen at the cathode to a specific amount by restricting the flow of ions in the electrolyte solution to and from the cathode with the hydrogen collector receptacle;
providing a delivery device that is connected to the hydrogen collector receptacle, and that delivers hydrogen gas to a user, the delivery device comprising a nasal cannula; and
transferring hydrogen collected in the hydrogen collector receptacle to the delivery device.

17. The electrolysis method of claim 16, wherein the specific amount of hydrogen gas collected in the hydrogen collector receptacle is less than about 4.5% of a user's breath.

18. The electrolysis apparatus of claim 9, wherein the concentration of hydrogen transferred to the delivery device is less than about 4.5% of the user's breath.

* * * * *